United States Patent [19]

Graf et al.

[11] 4,158,010
[45] Jun. 12, 1979

[54] PROCESS FOR PREPARING ORGANOSILANES

[75] Inventors: Werner Graf; Peter John; Volker Frey, all of Burghausen, Fed. Rep. of Germany

[73] Assignee: Wacker-Chemie GmbH, Munich, Fed. Rep. of Germany

[21] Appl. No.: 902,462

[22] Filed: May 3, 1978

[30] Foreign Application Priority Data

Jun. 23, 1977 [DE] Fed. Rep. of Germany ....... 2728196

[51] Int. Cl.² ............................................... C07F 7/12
[52] U.S. Cl. ............................................... 260/448.2 P
[58] Field of Search .................................. 260/448.2 P

[56] References Cited

U.S. PATENT DOCUMENTS

| 3,769,310 | 10/1973 | Viego et al. | 260/448.2 P |
|---|---|---|---|
| 3,793,357 | 2/1974 | McEntee | 260/448.2 P |
| 3,980,686 | 9/1976 | LeFort et al. | 260/448.2 P |

Primary Examiner—Paul F. Shaver

[57] ABSTRACT

An improved process for converting an organosilane which comprises reacting at least one silane (A) having the formula $$R_a SiCl_{4-a}$$

with at least one silane (B) which differs from silane (A) and has the formula $$R_b SiCl_{4-b}$$

in the presence of an organoaluminum compound having the formula $$R_c^1 AlY_{3-c}$$

and at least one silane (C) having the formula $$R_b H_c SiCl_{4-b-c}$$

and from 0.1 to 5 percent by weight based on the weight of silanes (A), (B) and (C) of a hydrogen halide, in which R is a hydrocarbon radical having from 1 to 10 carbon atoms and is free of aliphatic unsaturation, $R^1$ is an alkyl radical having from 1 to 4 carbon atoms, Y is selected from the group consisting of halogen, hydrogen or hydrocarbon radicals having from 1 to 10 carbon atoms which are bonded to the aluminum via oxygen and are free of aliphatic unsaturation, a is 2, 3 or 4, b is 0, 1, 2 or 3 and c is 1, 2 or 3 and the sum of b+c cannot exceed 4.

6 Claims, No Drawings

PROCESS FOR PREPARING ORGANOSILANES

The present invention relates to an improved process for preparing organosilanes and particularly to an improved process for preparing organosilanes by the redistribution reaction of silanes. More particularly the invention relates to an improved process for preparing organosilanes by reacting a mixture of halogen-containing silanes with silanes containing an Si-H bond in the presence of organoaluminum compounds and hydrogen halides.

BACKGROUND OF THE INVENTION

Heretofore, it was known that organosilanes could be converted by the redistribution reaction of silanes. For example, organosilanes can be converted by reacting at least one silane (A) of the formula:

$$R_aSiCl_{4-a}$$

with at least one silane (B) which differs from (A) and which corresponds to the general formula:

$$R_bSiCl_{4-b}$$

where R represents the same or different hydrocarbon radicals having from 1 to 10 carbon atoms which are free of aliphatic unsaturation and a is 2, 3 or 4 and b is 0, 1, 2 or 3. Also Noll, "Chemie und Technologie der Silicone", Weinheim, 1968, discloses at pages 51 and 52 that this type of reaction can be enhanced in the presence of catalysts. In this regard, U.S. Pat. No. 2,786,861 discloses a mixture of aluminum chloride and a silane having at least one Si-bonded hydrogen atom as being a suitable catalyst for the redistribution reaction. British Pat. No. 851,868 discloses that organoaluminum compounds having the general formula:

$$R_c^1AlY_{3-c}$$

may be used to convert organosilanes by the redistribution reaction, in which $R^1$ represents the same or different alkyl radicals having from 1 to 4 carbon atoms, Y represents halogen, hydrogen and hydrocarbon radicals having from 1 to 10 carbon atoms which are free of aliphatic unsaturation and are bonded to the aluminum atom via oxygen; and c is 1, 2 or 3. The processes known heretofore have several disadvantages. For example, the disadvantages of using aluminum chloride is described in British Pat. No. 851,868. Also British Pat. No. 915,479 discloses that hydrogen chloride exerts an undesirable influence on the redistribution reaction of silanes in the presence of a silane having Si-bonded hydrogen and aluminum chloride. German Patent Application No. 2,132,335 discloses a process for converting silanes which requires pressures above atmospheric pressure.

In comparison to the processes known heretofore, the process of this invention has several advantages. For example, the redistribution reaction can be carried out at atmospheric pressure. Also, the process can be carried out at low temperatures and in the presence of smaller quantities of aluminum compounds. Moreover, the disadvantages described in British Pat. No. 851,868 in using aluminum chloride are avoided in the present process. Furthermore contrary to the teachings of British Pat. No. 915,479, applicants have found that the presence of hydrogen halide in the present process does not exert an undesirable influence on the redistribution reaction of silanes.

Therefore it is an object of this invention to provide an improved process for preparing organosilanes. Another object of this invention is to provide an improved process for preparing organosilanes at atmospheric pressure. Still another object of this invention is to provide an improved process for preparing organosilanes at low temperatures and in the presence of smaller quantities of aluminum compounds. A further object of this invention is to provide an improved process for preparing organosilanes in the presence of hydrogen halides.

SUMMARY OF THE INVENTION

The foregoing objects and others which will become apparent from the following description are accomplished in accordance with this invention, generally speaking, by providing an improved process for preparing organosilanes by reacting at least one silane (A) having the general formula:

$$R_aSiCl_{4-a}$$

with at least one silane (B) which differs from (A) and corresponds to the formula:

$$R_bSiCl_{4-b}$$

in the presence of at least one organoaluminum compound having the formula:

$$R_c^1AlY_{3-c}$$

where R represents the same or different hydrocarbon radicals having from 1 to 10 carbon atoms which are free of aliphatic unsaturation, $R^1$ represents the same or different alkyl radicals having from 1 to 4 carbon atoms, and Y represents halogen, hydrogen or hydrocarbon radicals having from 1 to 10 carbon atoms which are bonded to the aluminum atoms via oxygen and which are free of aliphatic unsaturation, a is 2, 3 or 4 and b is 0, 1, 2 or 3, and c is 1, 2 or 3; the improvement which comprises conducting the reaction in the presence of at least one silane (C) having the general formula $$R_bH_cSiCl_{4-b-c}$$

in which R, b and c are the same as above with the proviso that the sum of b+c may not be more than 4; and in addition from 0.1 to 5 percent by weight based on the weight of silanes (A), (B) and (C) of a hydrogen halide.

DETAILED DESCRIPTION OF THE INVENTION

In the above described silanes, the hydrocarbon radicals represented by R and Y may be alkyl radicals such as the methyl, ethyl, n-propyl, isopropyl, n-butyl, sec-butyl and the 2-ethylhexyl radical, as well as the decyl radicals; cycloalkyl radicals, such as the cyclohexyl radical; aryl radicals such as the phenyl radical; aralkyl radicals, such as the benzyl radical; and alkaryl radicals such as tolyl radicals.

Individual examples of silanes corresponding to the following general formulas $R_aSiCl_{4-a}$ (A) and $R_bSiCl_{4-b}$ (B) are trimethylchlorosilane, dimethyldichlorosilane, methyltrichlorosilane, diphenyldichlorosilane, ethyltrichlorosilane, n-propyltrichlorosilane, phenyltrichlorosilane, n-pentyltrichlorosilane, sec-pentyltrichlorosilane, cyclohexyltrichlorosilane and methylethyldichlorosilane.

Other examples of silanes (A) having the general formula $R_aSiCl_{4-a}$ are tetramethylsilane and tetraphenylsilane.

The silane (B) having the general formula $R_bSiCl_{4-b}$ may also be tetrachlorosilane.

It is preferred that the silane (A) having formula $R_aSiCl_{4-a}$ be used in amounts of from 0.8 to 1.2 mol for each mol of silane (B) having the general formula $R_bSiCl_{4-b}$.

The previously cited examples of hydrocarbon radicals represented by R and Y having from 1 to 4 carbon atoms are fully applicable to the hydrocarbon radicals represented by $R^1$.

Another example of a hydrocarbon radical represented by $R^1$ and Y is the tert-butyl radical.

Examples of halogen atoms represented by Y are fluorine, chlorine, bromine, or iodine; however, chlorine is the preferred halogen atom because of its availability.

Examples of organoaluminum compounds which may be employed in the process of this invention are ethyl aluminum sesquichloroide, ethyl aluminum dichloride, trimethylaluminum, methyl aluminum sesquichloride, diethyl aluminum chloride, tri-n-propylaluminum, n-propyl aluminum dichloride, di-n-butyl aluminum hydride and ethyl aluminum sesquiethoxide. Organoaluminum compounds having a boiling point above 150° C. at 760 mm Hg (abs.) are preferred. Because of its availability, ethyl aluminum sesquichloride is the preferred organoaluminum compound.

When traces of water are excluded, good results are obtained even with 0.1 percent by weight, based on the total weight of silanes (A), (B) and (C), with a compound having the formula:

$$R_c^1AlY_{3-c}.$$

However from 0.8 to 1.6 percent by weight, based on the total weight of silanes (A), (B) and (C) of the compound having the formula $$R_c^1AlY_{3-c}$$

are preferred.

Larger amounts of the compound having the formula $$R_c^1AlY_{3-c}$$

may be used; however no particular advantages are observed.

Examples of silanes (C) having the general formula $R_bH_cSiCl_{4-b-c}$ are silane, methyldichlorosilane, dimethylchlorosilane, trichlorosilane and monochlorosilane.

It is preferred that silane (C) be used in an amount of from 0.5 to 15 percent by weight and more preferably from 2 to 6 percent by weight, based on the total weight of silanes (A) and (B).

Because of its availability, hydrogen chloride is the preferred hydrogen halide. However instead of hydrogen chloride of a hydrogen chloride mixture, it is possible to use hydrogen fluoride, hydrogen bromide and/or hydrogen iodide as well.

The process of this invention can be carried out at room temperature and at atmospheric pressure, i.e., at 760 mm Hg (abs.) or at approximately 760 mm Hg (abs.). Although higher temperatures such as for example up to 450° C. may be used to accelerate the process; it is preferred that the temperatures not exceed about 150° C. When higher temperatures are used because of the boiling points of the reactants, it is possible to use increased pressure and/or a solvent having a high boiling point which is inert with respect to the other components of the reactive mixture. It is possible to use, for example, a mixture of alkanes having a boiling point of at least 150° C. at 760 mm Hg. (abs.).

Whenever possible, the reaction should be conducted under anhydrous conditions, i.e., in the absence of water.

The process of this invention can be carried out batchwise or semi-continuously or as a continuous process.

In the following examples all percentages are by weight unless otherwise specified.

EXAMPLE 1

Into a 3-necked flask equipped with a stirrer, reflux condenser and a gas conduit, is introduced over a period of 5 minutes at room temperature and under constant agitation, 2 liters [measured at 20° C. and at 720 mm Hg (abs.) and thus 1.5 percent based on the total weight of the silanes used] of gaseous hydrogen chloride, into a mixture which consists of 88 grams (1 mol) of tetramethylsilane, 129 grams (1 mol) of dimethyldichlorosilane, 2 grams of methyldichlorosilane and 3 grams of ethyl aluminum sesquichloride. Stirring is continued for an additional 5 hours at room temperature. The composition of the reaction mixture is then determined by gas chromatography. The following results are obtained:

| | |
|---|---|
| Tetramethylsilane | 6 percent |
| Trimethylchlorosilane | 85.3 percent |
| Dimethyldichlorosilane | 8 percent |
| Methyldichlorosilane | 0.7 percentage |

EXAMPLE 2

Into a 3-necked flask equipped with a stirrer, reflux condenser and a gas conduit, is introduced over a period of 5 minutes, under constant agitation and at room temperature, one liter [measured at 20° C. and 720 mm Hg (abs.) and thus 0.62 percent based on the total weight of the silanes used] of gaseous hydrogen chloride, into a mixture consisting of 149.5 grams (1 mol) of methyltrichlorosilane, 108.5 grams (1 mol) of trimethylchlorosilane, 2.5 grams dimethylchlorosilane and 3 grams n-propylaluminum dichloride. Stirring is then continued for an additional 8 hours while the reactive mixture is heated under reflux. The resultant composition contains the following products as determined by gas chromotographic analysis.

| | |
|---|---|
| Trimethylchlorosilane | 8 percent |
| Dimethyldichlorosilane | 83.7 percent |
| Methyltrichlorosilane | 8 percent |
| Dimethylchlorosilane | 0.3 percent |

EXAMPLE 3

Into a 3-necked flask equipped with a stirrer, reflux condenser and a gas conduit, is introduced over a period of 5 minutes with constant agitation and at room temperature, 2-liters [measured at 20° C. and 720 mm Hg (abs.) and thus 0.94 percent based on the total weight of the silanes used], of gaseous hydrogen chloride, into a mixture consisting of 253 grams (1 mol) of diphenyldichlorosilane, 88 grams (1 mol) of tetramethylsilane, 3 grams of trichlorosilane and 3 grams diethylaluminum chloride. Stirring is continued for an additional 4 hours while the mixture is heated under reflux. Fractional distillation yields 30 grams of trimethylchlorosilane, 35 grams of phenyldimethylchlorosilane, 80 grams of diphenylmethylchlorosilane and 74 grams of triphenylchlorosilane.

EXAMPLE 4

Into a 3-necked flask equipped with a stirrer, reflux condenser and gas conduit, is introduced over a period of about 8 minutes with constant agitation and at room temperature, 2 liters [as measured at 20° C. and 720 mm Hg (abs.) and thus approximately 0.85 percent based on the total weight of the silane used], of gaseous hydrogen chloride, into a mixture consisting of 130 grams of methyltrichlorosilane, 4 grams of ethyl aluminum sesquichloride and 250 grams of the products obtained from the reaction of methylchloride with silicon in accordance with U.S. Pat. No. 2,380,995 to Rochow, which boil at 50° C. at 760 mm Hg (abs.), said reaction products consisting of a mixture containing 70 percent tetramethylsilane, 2.5 percent dimethylchlorosilane, 0.5 percent trichlorosilane and various hydrocarbon residues. Stirring is then continued for an additional 6 hours while the mixture is refluxed. Fractional distillation yields 275 grams of trimethylchlorosilane.

COMPARISON EXAMPLE 1

The process described in Example 1 is repeated, except that the hydrogen chloride is omitted. Gas chromatographic analysis of the resultant mixture reveals only approximately 1 percent trimethylchlorosilane.

COMPARISON EXAMPLE 2

The process described in Example 2 is repeated, except that the silane having Si-bonded hydrogen is omitted, Gas chromatographic analysis of the resultant mixture reveals less than 3 percent dimethyldichlorosilane.

What is claimed is:

1. An improved process for preparing organosilanes by reacting at least one silane (A) of the general formula:

$$R_a SiCl_{4-a}$$

with at least one silane (B) which differs from (A) and corresponds to the general formula:

$$R_b SiCl_{4-b}$$

in the presence of at least one organoaluminum compound having the general formula:

$$R_c^1 AlY_{3-c},$$

the improvement which comprises conducting the reaction in the presence of at least one silane (C) having the general formula:

$$R_b H_c SiCl_{4-b-c}$$

and from 0.1 to 5 percent by weight of hydrogen halide based on the weight of silanes (A), (B) and (C), in which R is a hydrocarbon radical free of aliphatic unsaturation and has from 1 to 10 carbon atoms; $R^1$ is an alkyl radical having from 1 to 4 carbon atoms; Y is selected from the group consisting of halogen, hydrogen and hydrocarbon radicals having from 1 to 10 carbon atoms which are free of aliphatic unsaturation and which are bonded to the aluminum atom via oxygen; a is 2, 3 or 4; b is 0, 1, 2 or 3; c is 1, 2 or 3 and the sum of b+c must not exceed 4.

2. The improved process of claim 1, wherein the hydrogen halide is hydrogen chloride.

3. The improved process of claim 1, wherein the reaction is conducted at room temperature and at atmospheric pressure.

4. The improved process of claim 1, wherein the reaction is conducted under anhydrous conditions.

5. The improved process of claim 1, wherein the organo aluminum compound is present in an amount of at least 0.1 percent by weight based on the weight of silanes (A), (B) and (C).

6. The improved process of claim 1, wherein the silane (C) is present in an amount of from 0.5 to 15 percent by weight based on the weight of silanes (A) and (B).

* * * * *